United States Patent [19]

Douglass

[11] 4,211,871

[45] Jul. 8, 1980

[54] HEAVY METAL DERIVATIVES OF MERCAPTOPYRIDINE-1-OXIDE

[75] Inventor: Miriam L. Douglass, Piscataway, N.J.

[73] Assignee: Colgate-Palmolive Company, New York, N.Y.

[21] Appl. No.: 932,065

[22] Filed: Aug. 8, 1978

Related U.S. Application Data

[62] Division of Ser. No. 791,613, Apr. 27, 1977, Pat. No. 4,122,084, which is a division of Ser. No. 629,436, Nov. 6, 1975, Pat. No. 4,048,181.

[51] Int. Cl.$^2$ .......................................... C07D 213/89
[52] U.S. Cl. ....................................................... 546/6
[58] Field of Search ............................................. 546/6

[56] References Cited

U.S. PATENT DOCUMENTS 4,009,168  2/1977  Masaki ...................................... 546/6

Primary Examiner—Mark L. Berch
Attorney, Agent, or Firm—Richard N. Miller; Murray M. Grill; Herbert S. Sylvester

[57] ABSTRACT

Heavy metal salts of 2-amino derivatives of 6-mercaptopyridine-1-oxide, including 2-acylamino- and 2-alkoxycarbonylamino-6-mercaptopyridine-1-oxide, having particular utility as antimicrobial agents per se and in skin cleansing detergent composition, shampoos, hair dressings, disinfectants, preservatives and the like.

6 Claims, No Drawings

HEAVY METAL DERIVATIVES OF MERCAPTOPYRIDINE-1-OXIDE

This is a divisional of application Ser. No. 791,613 filed Apr. 27, 1977, now U.S. Pat. 4,122,084 granted Oct. 24, 1978, which is a divisional of application Ser. No. 629,436 filed Nov. 6, 1975, now U.S. Pat. 4,048,181 granted Sept. 13, 1977.

This invention relates to substituted amino-containing mercapto-pyridine-1-oxide derivatives having both antibacterial and antifungal activity, methods of manufacturing these compounds and compositions containing them.

The art is replete with antibacterial agents and varied compositions containing such agents. Mercaptopyridine-1-oxide, the alkali metal and heavy metal salts thereof and disulfides thereof are known to possess antibacterial and anti-fungal activity. They have been found useful in a variety of antifungus and anti-bacterial compositions inclusive of weed killing plant or soil fungicides, nasal sprays, topical creams, topical dusting powder, shampoos, textile preservatives, etc. However, mercaptopyridine-1-oxide compounds wherein a substituted amino radical is attached to a carbon atom in the pyridine ring are not disclosed in the prior art. It has been found that these novel compounds possess the property of wide-spectrum anti-bacterial and anti-fungal activity per se as well as when incorporated into compositions such as preservatives, disinfectants, skin-cleansing detergents, shampoos, hair dressings and the like.

A particularly difficult medium for successful employment of an anti-microbial compound is the human scalp and the hair thereon. Due to continued secretions of sebum and perspiration and deposits of dust, grease and oils on the scalp, often in part at least attributable to the use of preparations for treating the scalp and hair, particularly favorable conditions for the growth of microorganisms often prevail on the scalp. Even if the hair and scalp are washed fairly frequently, growth of microorganisms there is generally faster than on most other parts of the human body and consequently the actions of antimicrobial compounds employed thereon are often ineffective. However, by the use of the compounds of this invention, good activity is obtained against microorganisms commonly found in the scalp and frequently associated with the dandruff syndrome.

The present compounds may be used in solutions, emulsions or suspensions, or as solids. They are usually in the form of aqueous solutions and may be applied to sites on which growth of microorganisms is to be counteracted. For ease of application to such sites, they may be included in various carrier compositions and are considered to be especially useful in hairdressing preparations and in shampoos.

In accordance with the present invention there are provided novel derivatives of mercaptopyridine-1-oxide having the following structural formula:

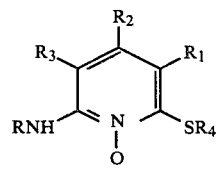

wherein R is selected from the group consisting of an acyl $R_oC=O$, where $R_o$ is a $C_1$-$C_6$ alkyl, aryl selected from the class consisting of naphthyl and benzyl, halosubstituted aryl, aralkyl, said alkyl having 1-6 carbons; an alkoxycarbonyl $R_oOC=O$, where $R_o$ has the same meanings as above; a $C_1$-$C_6$ alkanesulfonyl; an aralkanesulfonyl; an arenesulfonyl $ArSO_2$, wherein the aryl group may be substituted by a $C_1$-$C_6$ alkyl, alkoxy and/or a halo radical; $R_1$, $R_2$ and $R_3$ are independently selected from the group consisting of hydrogen, straight and branched chain $C_1$-$C_6$ alkyl groups, aryl and aralkyl groups, wherein the aryl group may be a phenyl, napthyl and furyl and may be substituted by a halo and/or a $C_1$-$C_6$ alkyl group; $R_4$ is selected from the group consisting of hydrogen, benzyl, and a metal from the group consisting of sodium, potassium, lithium, zinc, calcium, magnesium, manganese, chromium, iron, copper, tungsten, nickel, barium, strontium, a quaternary ammonium ion $R_5R_6R_7R_8N^+$ wherein $R_5$ and $R_6$ are each hydrogen or $C_1$-$C_3$ alkyl, $R_7$ is hydrogen, $C_1$-$C_3$ alkyl, benzyl or $C_{12}$-$C_{22}$ alkyl and $R_8$ is hydrogen, $C_1$-$C_3$ alkyl or $C_{12}$-$C_{22}$ alkyl, and the group:

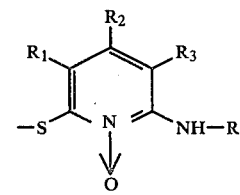

Related disulfides have the formula:

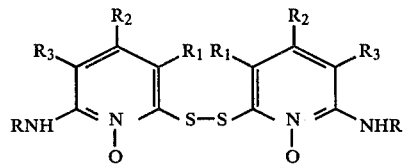

Salts of the mercaptopyridine-1-oxides have the formula:

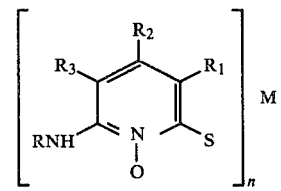

wherein R, $R_1$, $R_2$ and $R_3$ have the same meanings as in formula I, M is a mono-, di-, or trivalent metal selected from the group consisting of sodium, potassium, lithium, zinc, calcium, magnesium, manganese, chromium, iron, copper, tungsten, nickel, barium and strontium, and n is a number from 1 to 3. Specific examples are:
2-acetamido-6-mercaptopyridine-1-oxide,
2-ethoxycarbonylamino-6-mercaptopyridine-1-oxide,
2-propionamido-6-mercaptopyridine-1-oxide,
2-butanoamido-6-mercaptopyridine-1-oxide,
pentanoamido-6-mercaptopyridine-1-oxide,
2-hexanoamido-6-mercaptopyridine-1-oxide,
2-methoxycarbonylamino-6-mercaptopyridine-1-oxide,
2-propoxycarbonylamino-6-mercaptopyridine-1-oxide, 2-butoxycarbonylamino-6-mercaptopyridine-1-oxide,
2-pentoxycarbonylamino-6-mercaptopyridine-1-oxide,
2-hexoxycarbonylamino-6-mercaptopyridine-1-oxide,
2-methanesulfonylamino-6-mercaptopyridine-1-oxide,
2-ethanesulfonylamino-6-mercaptopyridine-1-oxide,
2-propanesulfonylamino-6-mercaptopyridine-1-oxide,
2-butanesulfonylamino-6-mercaptopyridine-1-oxide,
2-pentanesulfonylamino-6-mercaptopyridine-1-oxide,
2-hexanesulfonylamino-6-mercaptopyridine-1-oxide,
2-benzenesulfonylamino-6-mercaptopyridine-1-oxide,
sodium or cinc salt of 2-ethoxycarbonylamino-6-mercaptopyridine-1-oxide,
sodium or zinc salt of 2-acetamido-6-mercaptopyridine-1-oxide,
bis[2-(6-ethoxycarbonylamino-1-oxopyridyl)]disulfide,
2-acetamido-3(4 or 5)-methyl-6-mercaptopyridine-1-oxide,
2-ethoxycarbonylamino-3(4 or 5)ethyl-6-mercaptopyridine-1-oxide,
2-propionamido-3(4 or 5)-n-butyl-6-mercaptopyridine-1-oxide,
2-butanoamido-3(4 or 5)-methoxy-6-mercaptopyridine-1-oxide,
2-pentanoamido-3(4 or 5)-ethoxy-6-mercaptopyridine-1-oxide,
2-hexanoamido-3,5-dimethyl-6-mercaptopyridine-1-oxide,
2-methoxycarbonylamino-3(4 or 5)-methyl-5(3 or 4)ethyl-6-mercaptopyridine-1-oxide,
2-propoxycarbonylamino-3,5(or 3,4)-dimethoxy-6-mercaptopyridine-1-oxide,
2-butoxycarbonylamino-3,4,5-trimethyl-6-mercaptopyridine-1-oxide,
2-toluenesulfonylamino-6-mercaptopyridine-1-oxide,
cetyl trimethyl ammonium salt of 2-acetamido-6-mercaptopyridine-1-oxide,
cetyl trimethyl ammonium salt of any of the cited mercaptopyridine-1-oxides,
triethyl octadecyl ammonium salt of the cited mercaptopyridine-1-oxide compounds,
myristyldimethyl benzyl ammonium salt of the cited mercaptopyridine-1-oxides,
dimethyl dilauryl ammonium salt of above named mercaptopyridine-1-oxides,
2-acetamido-3(4 or 5)-phenyl-6-mercaptopyridine-1-oxide,
2-ethoxycarbonylamino-3(4 or 5)-furyl-6-mercaptopyridine-1-oxide,
2-acetamido-3(4 or 5)-naphthyl-4(3 or 5)methyl-6-mercaptopyridine-1-oxide,
2-acetamido-3(4 or 5)-bromophenyl-6-mercaptopyridine-1-oxide,
2-acetamido-3(4 or 5)-chlorophenyl-6-mercaptopyridine-1-oxide,
2-acetamido-3(4 or 5)-(trichlorophenyl)-6-mercaptopyridine-1-oxide,
2-acetamido-3(4 or 5)-chlorobenzyl-6-mercaptopyridine-1-oxide,
2-acetamido-3(4 or 5)-(dichlorobenzyl)-6-mercaptopyridine-1-oxide,
2-p-chlorobenzamido-6-mercaptopyridine-1-oxide,
2-benzamido-6-mercaptopyridine-1-oxide,
2-phenoxycarbonylamino-6-mercaptopyridine-1-oxide, These mercaptopyridine-1-oxide derivatives are generally prepared in three steps: Step 1-Forming the substituted aminobromopyridine by reacting 2-amino-6-bromopyridine with a reactant containing the substituent R. In lieu of the 2-amino-6-bromopyridine reactant, the pyridine nucleus may have substituents on the 3,4 or 5 carbons from the class consisting of $C_1-C_6$ alkyl groups; aryl groups such as phenyl, naphthyl furyl, $C_1-C_6$ alkyl and/or halo-substituted aryl groups; and $C_1-C_6$ aralkyl groups, wherein the aryl group has the same definition as above.

The lower aliphatic acid anhydride or acid halide such as the chloride or bromide containing 1-7 carbon atoms is suitable in the formation of the acylamino derivatives. Examples of these reactants are acetic anhydride, acetyl chloride, propionic acid chloride, propionic acid anhydride, butyric acid anhydride, butyric acid chloride, valeric acid anhydride, valeric acid chloride, hexanoic acid anhydride, heptanoic acid anhydride, heptanoic acid chloride and the like. The corresponding acylaminobromo-pyridine is obtained. The acid anhydride or acid chloride, being liquid, is used both as the reactant and solvent for the reaction. The alkoxycarbonylamino-bromopyridine is obtained by utilizing a lower alkyl halo-formate inclusive of the chloro- and bromo-formates as the reactant in lieu of the acid anhydride or acid halide. Suitable halo-formates include methyl chloroformate

ethyl chloroformate, propyl chloroformate, butyl chloroformate, hexyl chloroformate, pentyl chloroformate, and the corresponding bromo-formates. Similarly the $C_1-C_6$ alkanesulfonylamino-bromopyridines may be obtained by using a lower alkanesulfonyl ($RSO_2$) containing reactant such as an alkanesulfonic acid anhydride or acid chloride. Likewise, the arenesulfonyl amino-bromopyridine can be obtained by using an arenesulfonyl

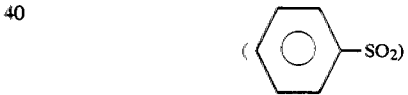

halide or other reactive arenesulfonyl compound.

Step 2: The above reaction product is oxidized with an organic peracid such as peracetic acid, m-chloroperbenzoic acid and the like, to form the corresponding amino-substituted pyridine-1-oxide.

Step 3: Forming the mercaptopyridine-1-oxide compound by reacting the amino substituted pyridine-1-oxide compound with an alkali metal hydrosulfide such as sodium hydrosulfide. The respective salts thereof are prepared by reacting the mercapto derivative with sodium hydroxide, sodium methoxide, zinc nitrate or any other metal salt desired. The disulfides are prepared by reacting the mercapto derivative with iodine, potassium triiodide or dilute hydrogen peroxide or other oxidizing agent.

The amino derivatives of mercaptopyridine-1-oxide may be generally prepared by reacting a 2-amino-6-bromopyridine compound with an excess amount of acid anhydride or acid halide containing the R substituent, in the presence of a suitable solvent such as acetic anhydride, glacial acetic acid, at elevated temperatures of about 50°-75°, preferably at 55°-60° C., for about 30 minutes to five hours, with continuous agitation to form the corresponding 2-acylamino-6-bromopyridine, which may be purified by recrystallization from benzene. Another method of preparing the amino derivative of 6-bromopyridine comprises reacting a 2-amino-6-bromopyridine with an excess amount of an alkyl haloformate containing the R constituent in the presence of a suitable solvent such as pyridine, while cooling to a temperature of about 15°–30° C. (exothermic reaction) with continuous agitation, for a period of about 30 minutes, to obtain the corresponding 2-alkoxycarbonylamino-6-bromopyridine, which may be purified by recrystallization from an aqueous methanol solution. The resultant pyridine compound, dissolved in a suitable solvent such as acetic acid, benzene, chloroform (as determined by the oxidizing agent), is subsequently oxidized with an excess amount of peracid such as peracetic, perbenzoic, chloroperbenzoic acid, at elevated temperatures of about 50°–75° C. for about 3 to 24 hours, with continuous agitation to form the pyridine-1-oxide derivative, which may be purified by recrystallizing from propanol, cyclohexane, chloroform, or other suitable solvent. The resultant pyridine-1-oxide compound is reacted with an excess amount of an aqueous hydrosulfide salt at elevated temperatures of 50°–75° C., preferably 60° C., for a period of 2 to 5 hours, to form the corresponding mercaptopyridine-1-oxide compound, which may be purified by recrystallization from propanol, aqueous ethanol and the like.

The salts of the amino-substituted mercaptopyridine-1-oxides are prepared by neutralizing the aforesaid mercaptopyridine-oxides with an aqueous solution of a suitable base to a pH of about 5–8, at room temperature, and subsequently adding an aqueous solution of the desired metal or quaternary ammonium salt.

The disulfides are prepared by reacting the aminosubstituted-mercaptopyridine-1-oxide compound per se or the sodium salt thereof with an oxidizing agent such as potassium triiodide, iodine, or hydrogen peroxide, in an aqueous medium and at room temperature.

The benzylthio derivative of the amino-substituted pyridine-1-oxide is prepared by reacting the amino-substituted-6-bromo-pyridine-1-oxide with benzyl mercaptan in a suitable solvent such as methanol containing sodium methoxide, by heating to a temperature of about 55°–80° C. for about two hours, with continuous agitation. The resultant benzylthio derivative may be purified by recrystallization from ethyl acetate and cyclohexane.

More specifically, the mercapto pyridine-1-oxide derivatives of the instant invention are prepared from known starting materials. 2-amino-6-bromopyridine which may be prepared by hydrogen bromide induced cyclization of 3-hydroxyglutaronitriles, a method described in U.S. Pat. No. 3,096,337, or by any other known process, is dissolved in an excess amount of acetic anhydride and heated at 70° C. for 45 minutes and the excess acetic anhydride is hydrolyzed by the addition of 300 ml. water, to give a substantially quantitative yield (95%) of 2-acetamido-6-bromopyridine which has a melting point of 159.2°–160.0° C. The 2-acetamido-6-bromopyridine is oxidized by heating a solution thereof in glacial acetic acid with an excess of peracetic acid at 70° C. for 2 hours and at 55° C. for 19 hours. The reaction mixture is diluted with 1600 ml. water and concentrated in vacuum, unreacted material removed by filtration, and the solvent evaporated from the filtrate, giving an 83% yield of impure 2-acetamido-6-bromopyridine-1-oxide which is purified and recrystallized from 2-propanol to yield fine white needles having a melting point of 180.0°–180.5° C. The mercapto derivative of 2-acetamido-5-bromopyridine-1-oxide may be prepared by reaction with an excess of sodium hydrosulfide (1 M NaSH) in an aqueous-ethanol medium while stirring for 5 hours at 60° C. and overnight at room temperature, adding concentrated hydrochloric acid dropwise to the cold yellow solution and collecting the light yellow solid by filtration, purifying by recrystallization from 2-propanol and obtaining pale yellow crystals having a melting point of 172.8°–173.5° C. A 79% yield of 2-acetamido-6-mercaptopyridine-1-oxide is obtained with the aforedefined process.

The alkali metal salt of 2-acetamido-6-mercaptopyridine-1-oxide is prepared by alkalization with a base such as sodium hydroxide, or potassium hydroxide, or ammonium hydroxide or the salt of the alkali metal with a weak acid (e.g., sodium carbonate) in an aqueous or aqueous-alcoholic medium. Various other metal salts, such as alkaline earth metals, zinc, etc. of instant mercaptopyridine-1-oxides may be obtained in yields of 65–95% by dissolving the amino substituted mercapto pyridine-1-oxide compound or the sodium salt thereof in water, adjusting the pH to about 5, adding an aqueous solution of the desired metal salt, (e.g., metal nitrate, halide, sulfate, etc.), purifying the precipitate by successively washing with water, ethyl alcohol and/or ethyl ether.

The reactions described above are illustrated by the following equations:

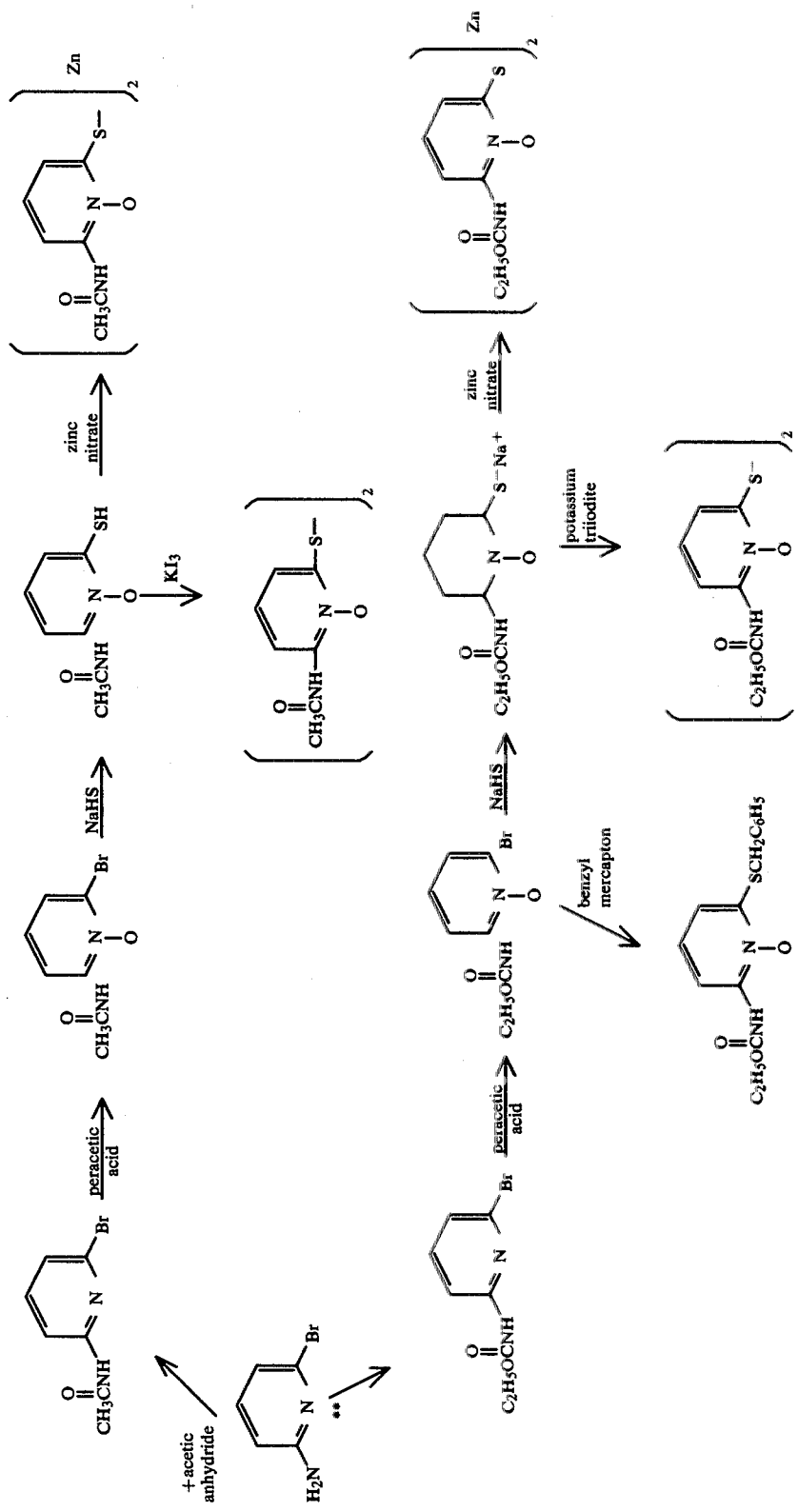

For clarity of presentation, the above description of methods of making the invented compounds has been given with respect to a particular starting material and corresponding derivatives thereof. However, it must be realized that such methods are also applicable to reactions utilizing different starting materials and effected by different reagents, which are equivalent in their activities to those described. Thus, instead of utilizing 2-amino-6-bromopyridine as the starting material, compounds having either branched or straight chain $C_1$–$C_6$ alkyl groups or aryl groups such as phenyl, napthyl, furyl, $C_1$–$C_6$ alkyl and/or halo-substituted aryl groups or $C_1$–$C_6$ aralkyl groups wherein said aryl group is as aforedefined, bonded to the pyridine nucleus at the 3-, 4-, and/or 5- position, may also be employed as the starting material. Similarly, the bromide anion may be replaced by another negatively charged inorganic or organic group such as chloride, fluoride, or iodide, with the bromide and chloride being preferred. Catalysts may be used, if desired. The solvents to be employed will be such as are conducive to dissolving the reagents and which are unaffected by the reaction.

The salt of the substituted amino-mercaptopyridine-1-oxide may be converted to the corresponding mercaptopyridine-1-oxide compound by treatment with any suitable chemical for removing the salt-forming cation and replacing it with hydrogen. Thus, usually an aqueous solution of an acid, preferably a dilute solution of a strong inorganic acid such as hydrochloric acid or sulfuric acid, may be used to precipitate the amino-mercaptopyridine-1-oxide compound. The stoichiometric quantity of acid, plus or minus 20%, will normally be employed and its dilution will usually be such that the normality is from 1 to 6 Normal. Of course, variations may be made in the types of acid and the concentrations employed, provided that sufficient acid is used to convert the salt to the acid form. Other salts of the amino-substituted mercaptopyridine-1-oxides may be obtained by treatment of a soluble salt thereof with a soluble metal, ammonium or quaternary ammonium or other suitable inorganic or organic salt. If the alkali metal salt is more soluble, it will often be possible to convert to other salts, such as heavy metal salts, merely by addition of a soluble heavy metal salt to the alkali metal salt of the amino-substituted mercaptopyridine-1-oxide, preferably in aqueous solutions. Again, it is preferred to employ approximately stoichiometric proportions of such salt and the corresponding alkali metal salt of said mercaptopyridine-1-oxide, but variations usually plus or minus 10 to 20% from stoichiometric proportions, are also useful. Among the salts that may be made from the alkali metal salts, e.g., the sodium, potassium and lithium salts of the acylamino or alkoxycarbonylamino mercaptopyridine-1-oxide, are the zinc, calcium, magnesium, manganese, chromium, iron, copper, tungsten, nickel, barium, strontium, ammonium and quaternary ammonium, e.g., cetyltrimethyl ammonium, triethyloctadecyl ammonium, myristyl dimethyl benzyl ammonium, methyl dilauryl ammonium, ethyldimethylstearyl ammonium, benzyldimethylstearyl ammonium, trimethylstearyl ammonium, dimethylpropyl myristyl ammonium, etc. The salts that may be employed include the corresponding chlorides, bromides, iodides, sulfates, phosphates, carbonates, borates, nitrates, acetates, citrates, propionates, phenates, and the other useful water soluble salts.

From the substituted amino mercaptopyridine-1-oxides, there may be produced the corresponding bis[6-(2-substituted amino-1-oxypyridyl)] disulfide by oxidation. In such oxidation as shown by the equations, hydrogen atoms adjacent to the sulfur of the corresponding mercaptopyridine-1-oxide are removed, to be combined with oxygen to form water. Thus, the sulfur atoms bond together, forming the disulfide. Such oxidation may be effected by any suitable means, preferably utilizing potassium triiodide, iodine, hydrogen peroxide, or other oxidizing agent. The substituted-amino mercaptopyridine-1-oxide compound is usually dissolved or suspended in a suitable solvent which is capable of maintaining its liquid form during the reaction. The proportion of reactant in solvent is not considered to be critical. The preferred substituted amino groups include the acylamino-, and the alkoxycarbonylamino radicals.

The compounds produced, whether in the form of the substituted-amino-mercaptopyridine-1-oxide compound, the disulfide thereof, or a salt thereof, exhibit exceptionally good antimicrobial properties. They are found to have wide-spectrum antibacterial activity and to be effective in killing bacteria and in limiting the growths of a variety of organisms. Particularly, they are very effective against the organism *Pityrosporum ovale*, commonly found on the scalp and frequently associated with the dandruff syndrome. A 10% suspension of 2-ethoxycarbonylamino-6-mercaptopyridine-1-oxide in 95% ethanol has been found to inhibit the growth of *P. ovale* in an amount as low as 1.9 micrograms per milliliter. Similarly, a 1.0% suspension of the disulfide of the above compound in 95% ethanol inhibits the growth of *P. ovale* in an even lower amount, namely, less than 0.5 micrograms per milliliter. Whereas from 1.9 to 12.5 micrograms per milliliter of the zinc salt of 2-mercaptopyridine-1-oxide (a known antimicrobial agent) is required to inhibit the growth of *P. ovale*. Thus, it is apparent that the acylamino substituted mercaptopyridine oxides of instant invention exhibit greater toxicity against *Pityrosporum ovale*, an organism commonly found with hair and scalp associated with dandruff. Often, when microorganisms are growing in such an environment, it is difficult to have an antimicrobial compound be effective against them, due to the inhibiting action of the grease or lipophilic material on the bactericide. Such inhibition may be either chemical or physical, whereby the lipophile reacts with the antimicrobial compound to change it to a less effective compound, or in which it prevents contact of the antimicrobial product with the microorganism.

In addition to the excellent utilities of the present compounds in such difficult environments, which are encountered on human or animal bodies and on the scalp or hair, it is found that these compounds are compatible with a wide variety of compositions and media in which they are employed. Thus, aqueous and alcoholic solutions of these compounds are useful, as are cosmetic preparations containing them, whether based on aqueous or lipophilic media or combination of both such phases. For example, the present antimicrobial compounds may be used in cosmetics or detergents, including liquid, solid, and semisolid paste, cream or gelatinous preparations. They may be employed in soaps, shampoos, hairdressings, dusting powders or talcs, foot powders, "aerosol" spray preparations of various types, anti-perspirants, deodorants, antisepetics and many other materials intended for cleaning, grooming or sanitizing purposes. Perhaps the most preferred compositions containing these compounds are those which are used in contact with the human hair or scalp, such as shampoos and hairdressings. Water or alcohol-soluble active ingredients are necessary for the formulation of transparent anti-dandruff hair products. The solubility at pH 7 of certain of instant substituted-amino mercaptopyridine-1-oxide compounds and the sodium salts thereof exceeds 0.5–1% and thus is suitable for hair dressings and shampoos. Others, such as the zinc salts of the substituted amino-mercaptopyridine-1-oxides are insoluble and thus amenable to formulation only in opaque products. After use of such preparations, it appears that the effects of the present anti-microbial compounds are long lasting. The substituted amino mercaptopyridine-1-oxides, disulfides, and salts thereof, are effective against such potent gram-positive organisms as *Staphylococcus aureus, Streptococcus mitis,* gram negative bacteria such as *Escherichia coli, Pseudomonas seruginosa,* as well as against the yeasts such as *Candida albicans* and *Pityrosporum ovale* and the molds *Trichophyton mentagrophytes* and *Aspergillus niger.*

A high level of activity against the mold *Trichophyton mentagrophytes,* and the yeast most frequently associated with dandruff, *Pityrosporum ovale,* is exhibited by the compounds of instant invention. Such effects of these compositions have not been noted before and the active antibacterial compounds and compositions containing them have not been taught or suggested by the prior art.

In addition to the new compounds and methods for their manufacture, also within the present invention, are cosmetic and detergent compositions containing such compounds as active wide-spectrum antimicrobial ingredients, and antimicrobial uses of the compounds and such compositions. It is considered that the present antimicrobials are useful in a wide variety of cosmetic preparations, including hairdressings, hair tonics, hair waving solutions, hair dyes, bleaches, rinses, face creams, face powders, foot powders, body lotions, tanning agents, antiperspirants, sunscreens, personal deodorants, makeup preparations, bath oils, facial treatments, astringents, shaving creams, after-shave lotions and various other preparations for treatment of the hair or skin, in which antibacterial or antifungal activity is useful. Among the detergent compositions which can usefully include the present antimicrobial compounds are bar soaps, liquid soaps, soap shampoos, synthetic detergent shampoos, heavy duty synthetic organic detergents, inorganic detergent salts, pre-soak compositions, which may include enzymes, softeners, dishwashing products, synthetic detergents intended for washing hard surfaces, e.g., jantorial detergents, floor cleaning compositions and other detergent-related products such as wax-removers, organic solvent solutions of surface active materials, compositions for employment with steam cleaning machinery, car washes, and sterilizing preparations.

The cosmetic compositions may contain from 0.1 to 99% of active ingredients for the primary purpose for which they are intended, together with from 0.1 to 10%, preferably from 0.1 to 3%, of a compound of the present invention. Usually the cosmetics will contain from 1 to 100% of an aqueous or an oily phase or a solid material (foot and face powders), and sometimes, as in the case of emulsions, will contain both aqueous and oily phases, often with a surface active material to aid in emulsification. Such surface active agents may be anionic, nonionic, cationic or amphoteric and are usually present in emulsified cosmetics in proportions of from 0.5 to 20% thereof.

Although the most preferred embodiments of the invention, hairdressings or other preparations intended for application to the hair, may be essentially lipophilic, essentially hydrophilic or emulsions, and may even be inert powders, the present compounds may be employed in any such medium. If the medium is lipophilic, there will usually be present from 50 to 99% of oil, such as mineral oil, lanolin, lanolin derivatives or other lipophilic materials, together with one or more of the present compounds. A solvent, e.g., a lower alkanol such as ethanol or isopropanol, may also be used to thin the lipophilic phase to make it easier to apply. It will usually be from 5 to 80% of the cosmetic. If the preparation is hydrophilic, it will usually contain from 50 to 99% of water, sometimes with 5 to 50% lower alkanol solvent associated therewith, plus one or more of the present anti-microbial compounds. The emulsions may have from 1 to 99%, usually from 20 to 80% of either lipophilic or hydrophilic materials, with essentially the balance thereof being of the other type. The various active ingredients utilized to give the different cosmetic preparations their desired properties are well known and are exhaustively described in the text by Edward Sagarin, Cosmetics Science and Technology (1957), and therefore will not be listed here. However, for example, it is mentioned that with respect to hairdressings, ordinarily a mineral oil and lanolin will be employed to condition the hair and facilitate its taking of waving and combing.

Antiperspirants will normally contain an active chemical for such purpose, such as aluminum chlorhydrate. Dusting powders will normally be based on talc, silica or other special form of such materials, such as pyrogenic silica. Skin creams or lotions will usually include stearic acid or other cold cream ingredients. The proportions of such active materials as was previously mentioned, may be varied widely, as is known in the art, and may constitute from 0.1 to 99% of the total composition.

The detergent compositions in which the present antimicrobial compounds are useful may be either built or unbuilt products and may be based on anionic, cationic, nonionic and/or amphoteric surface active compounds. These are well known and are described in the text by Schwartz, Perry and Berch, Surface Active Agents and Detergents, Volume II, (1958), particularly at pages 321 and 621–625. Most frequently, the detergents employed will be anionic detergents, including the common higher fatty acid soaps of alkali metals and the synthetic anionic organic detergent salts such as those which are currently commercially used.

As examples of the anionic synthetic organic detergents there may be mentioned the $C_{10}$–$C_{20}$ alkane sulfonates, $C_8$–$C_{18}$ fatty acid monoglyceride sulfates, linear $C_{10}$–$C_{15}$ alkyl benzene sulfonates, $C_8$–$C_{18}$ fatty acid soaps, $C_{10}$–$C_{15}$ alkyl polyoxyethylene (1–5EO) sulfates, hydroxyalkylene sulfonates, $C_8$–$C_{18}$ alcohol sulfates, salts of $C_1$–$C_3$ alcohol esters of $C_8$–$C_{18}$ sulfofatty acids, $C_8$–$C_{12}$ alkylphenol polyethoxy ether sulfates, $C_8$–$C_{18}$ acyl sarcosinates, $C_8$–$C_{18}$ acyl esters of isethionates and $C_8$–$C_{18}$ acyl N-methyl taurides, to name only a few. The salt-forming metals or other suitable salt-forming radicals for the detergents are preferably alkali metal, such as potassium or sodium, but alkaline earth metals such as calcium and magnesium and ammonium, alkylamine, and alkanolamine salts may also be used. Some specific examples of these detergents are sodium lauryl sulfate; sodium linear tridecyl benzene sulfonate, triethanolamine lauryl sulfate; sodium or potassium coconut oil—tallow soaps; sodium lauryl sulfonate; potassium hexadecylnaphthalene sulfonate; lauryl alcohol ethylene oxide sulfate comprising four ethoxy groups per molecule; potassium stearyl glyceryl ether sulfonate; sodium lauroyl sarcosinate; and magnesium methyl tauride.

Among the nonionic surface active agents are the condensation products of $C_8$–$C_{12}$ alkylated phenols with ethylene oxide, $C_8$–$C_{18}$ alkylthioethanols with ethylene oxide, $C_8$–$C_{18}$ fatty alcohols with ethylene oxide and polypropylene glycols or other polyols with ethylene oxide, wherein from 5 to 30 moles of ethylene oxide are associated with the hydrophobic moiety.

Among the cationic surface active materials are N-2-aminoethyl-higher alkyl amines; N-2-aminoethyl higher fatty acid amides; and quaternary ammonium compounds wherein an alkyl group is of 12 to 18 carbon atoms and other groups attached to the nitrogen are alkyls of 1 to 3 carbon atoms. Among such are ethyl-dimethylstearyl ammonium chloride; benzyl dimethylstearyl ammonium chloride; and trimethylcetyl ammonium bromide.

The amphoteric detergents, useful herein, are generally water soluble salts of derivatives of aliphatic amines which contain at least one cationic group which may be part of a heterocyclic ring, and an anionic water-solubilizing carboxyl, sulfo, sulfate, phosphate or phosphoro group in their molecular structure. Examples of suitable amphoteric detergents include the $C_8$–$C_{18}$ alkyl beta-aminopropionates, $RN(H)C_2H_4COOM$; the $C_8$–$C_{18}$ alkyl beta-iminodipropionates, $RN(C_2H_4COOM)_2$; the $C_8$–$C_{18}$ alkyl and hydroxyalkyl taurinates, $RN(CH_3)C_2H_4SO_3M$; and long chain ($C_7$–$C_{17}$) imidazole derivatives having the following formulas:

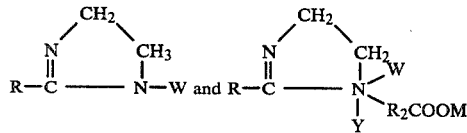

wherein W is selected from the group of

ROH, $R_2COOM$, and $R_2OR_2COOM$,

Y is selected from the group containing $OH^-$, $R_3O$-$SO_3^-$; $R_2$ is an alkylene or hydroxyalkylene group containing 1 to 4 carbon atoms; and M is a water soluble cation such as sodium, potassium, ammonium or alkylolammonium. Preferred detergents are sodium N-lauryl beta-amino-propionate, disodium N-lauryl iminodipropionate, and the disodium salt of 2-lauryl-cyclomidium-1-hydroxyl, 1-ethoxy-ethanoic acid, 1-ethanoic acid.

Zwitterionic detergents such as the betaines and sulfobetaines having the following formula are also useful:

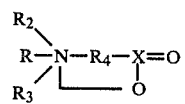

wherein R is an alkyl group containing about 10 to 18 carbon atoms, $R_2$ and $R_3$ are each $C_1$–$C_3$ alkyl, $R_4$ is an alkylene or hydroxyalkylene group containing about 1 to 4 carbon atoms, and X is C or S:O. The alkyl group can contain one or more intermediate linkages such as amido, ether or polyether linkage, or non-functional substituents such as hydroxyl or halogen which do not substantially affect the hydrophobic character of the group. When X is $C_1$, the detergent is called a betaine; and when X is S:O, the detergent is called a sulfobetaine or sultaine. Preferred betaine and sulfobetaines are 1-(lauryl dimethylammonio)acetate, 1(myristyl dimethyl ammonio)propane-3-sulfonate, and 1-(myristyl dimethylammonio)-2-hydroxy-propane-3-sulfonate.

In the built detergents, water soluble inorganic salt builders or organic builders are present to assist in dispersing peptizing, sequestering, and alkalizing, whereby detergency is increased. Among these are the pyrophosphates, tripolyphosphates, silicates, borates, carbonates, sequisilicates and other water soluble alkaline salts, for which the salt-forming metal is usually an alkali metal, such as sodium or potassium.

Generally, in the detergent compositions, the proportion of detergent will be from 5 to 99% by weight and preferably there will be present from 10 to 50% thereof in both built and unbuilt compositions. The builder salts, when present, will normally be from 15 to 60% by weight of the composition and the active antimicrobial compound will be from 0.1 to 10% thereof, preferably from 0.1 to 5% thereof and most often will be from 0.5 to 3% of the total product. Such compositions will usually include an adjuvant or mixture thereof, in an amount from 0.1 to 25% by weight. Such adjuvants include perfumes, dyes, bleaches, softening agents, antiredeposition agents, emollients, and brighteners. In the preferred detergents, which are essentially unbuilt shampoo preparations, there will be present from 5 to 33% of soap or synthetic organic detergent or mixture thereof, from 0.1 to 5% of antimicrobial compounds and from 1 to 20% of various adjuvants, such as thickeners, foaming agents, perfumes, coloring materials, and conditioning agents. The balance will be an aqueous medium such as water or a mixture of water with 5 to 25% by weight of a $C_1$–$C_3$ alkanol, if desired.

The present antimicrobial preparations, cosmetics or detergents are used in accordance with normal techniques. Thus, to sterilize or make antibacterial a particular surface, a suitable solution of the present amino derivatives of mercaptopyridine-1-oxide or other compound of this invention may be applied to the surface and allowed to remain there or it may be removed by rinsing after a suitable time. The detergents and cosmetics are used in normal fashion. The amino derivatives of mercaptopyridine-1-oxide, disulfides thereof, and salts thereof, act to kill bacteria and fungi while on the surface which is a locus thereof. Various of the present compounds are found to be especially useful against bacteria and fungi which normally are resident in the hair, such as *Staphylococous aureus* and *Pityrosporum ovale*.

The following examples are given to illustrate specific preferred embodiments of this invention. Clearly, the invention is not limited thereto. All temperatures are given in degrees centigrade and all parts are by weight, unless otherwise indicated.

EXAMPLE 1

Preparation of 2-acetamido-6-mercaptopyridine-1-oxide:

Step 1: 20 g (0.116 mole) of 2-amino-6-bromopyridine was dissolved in 140 ml. acetic anhydride and heated at 70° C. for 45 minutes. 2-Acetamido-6-bromopyridine was isolated by filtration as white flakes, m.p=159.2°-160.0° C., in 68% yield. The excess acetic anhydride present in the reaction mixture was hydrolyzed by the addition of 300 ml. water to the filtrate; the reaction mixture was agitated and an additional 27% yield of 2-acetamido-6-bromopyridine was collected by filtration, giving a 95% yield of reaction product, 2-acetamido-6-bromopyridine which was recrystallized from benzene.

| Elemental Analysis: | C | H | N |
|---|---|---|---|
| Calculated: | 39.10 | 3.28 | 13.02 |
| Found: | 39.12 | 3.24 | 13.09 |

Infrared characteristics (IR), absorption wave length in microns:
N—H; 3.13, 3.31
C=O; 6.02

Step 2: 23.4 gms (0.109 mole) of 2-acetamido-6-bromopyridine was dissolved in 200 ml. of glacial acetic acid containing 27.6 ml (0.218 mole) of 7.9 M peracetic acid and the solution was heated at 70° C. for 2 hours and at 55° C. for 19 hours. The reaction mixture was diluted with 1600 ml water and the solution was then concentrated in vacuo to 550 ml. 8.6% of unreacted-2-acetamido-6-bromopyridine was removed by filtration. The solvent was evaporated from the filtrate giving an 83% yield of impure 2-acetamido-6-bromopyridine-1-oxide which was purified by treatment with activated charcoal to remove the yellow impurity and subsequently recrystallized from 2-propanol. A second recrystallization from 2-propanol gave fine white needles, m.p=180.0°-180.5° C.

| Elemental Analysis: | C | H | N |
|---|---|---|---|
| Calculated: | 36.39 | 3.05 | 12.12 |
| Found: | 36.20 | 3.00 | 11.84 |
| IR: N—H; 3.08 | | | |
| C=O; 5.92 | | | |
| N—O; 8.23 | | | |

Step 3: 2 gms (0.0087 mole) of 2-acetamido-6-bromopyridine-1-oxide was suspended in 35 ml (0.035 mole) of 1 M aqueous sodium hydrosulfide and 30 ml of ethanol and agitated at 60° C. for 5 hours and at room temperature one night. Concentrated hydrochloric acid was added dropwise to the cold yellow solution and the precipitated solid filtered, giving a 79% yield of 2-acetamido-6-mercatopyridine-1-oxide. This impure product was purified by recrystallization from 2-propanol and hot filtration to remove a small amount of contaminating sulfur to give pale yellow crystals, m.p.=172.8°-173.5° C.

| Elemental Analysis: | C | H | N | S |
|---|---|---|---|---|
| Calculated: | 45.64 | 4.38 | 15.21 | 17.40 |
| Found: | 45.32 | 3.64 | 15.48 | 16.84 |
| I.R.: N—H; 3.09 | | | | |
| C=O; 5.91 | | | | |
| N—O; 8.31 | | | | |

EXAMPLE 2

Preparation of the zinc salt of 2-acetamido-6-mercaptopyridine-1-oxide:

0.50 M aqueous sodium hydroxide was added to 0.251 g (0.00136 mole) of 2-acetamido-6-mercaptopyridine-1-oxide, as prepared in Example 1, in 3 ml of water until a pH of 5 was obtained by said solution. 4.0 ml (0.0080 mole) of 0.20 M aqueous zinc nitrate was added to said solution, whereby the zinc salt of 2-acetamido-6-mercaptopyridine-1-oxide precipitated immediately. Upon filtration, an 84% yield of the zinc salt was obtained.

| Elemental Analysis: | C | H | N | S |
|---|---|---|---|---|
| Calculated: | 38.94 | 3.27 | 12.98 | 14.85 |
| Found: | 38.69 | 3.12 | 23.85 | 14.78 |
| I.R.: N—H; 3.04 3.13 | | | | |
| C=O; 5.91 | | | | |
| N—O; 8.06 | | | | |

EXAMPLE 3

Preparation of the sodium salt of 2-ethoxycarbonylamino-6-mercaptopyridine-1-oxide:

Step 1: 10.0 g (0.0578 mole) of 2-amino-6-bromopyridine was dissolved in 40 ml dry pyridine and 6.4 ml (0.067 mole) of ethyl chloroformate was added dropwise while the solution was stirred and cooled in an ice-bath to maintain the reaction temperature at 15°-18° C. After 4 hours at room temperature, the reaction mixture was poured into 150 ml of ice water and kept at 0° C. overnight. Impure 2-ethoxycarbonylamino-6-bromopyridine was obtained by filtration and subsequently recrystallized from 2:1 methanol-water solution, giving an 88% yield of white solid, m.p=70.2°-71.0° C.

| Elemental Analysis: | C | H | N |
|---|---|---|---|
| Calculated: | 39.21 | 3.70 | 11.43 |
| Found: | 38.92 | 3.66 | 11.45 |
| I.R.: N—H; 3.08 | | | |
| C=O; 5.85 | | | |

Step 2: A suspension of 2.0 g (0.00816 mole) of 2-ethoxycarbonylamino-6-bromopyridine in 10 ml of glacial acetic acid containing 1.3 ml (0.0102 mole) of 7.9 M peracetic acid was heated at 70° C. for 17 hours. The light yellow reaction mixture was cooled and diluted with 70 ml water and 8.5% of unreacted 2-ethoxycarbonylamino-6-bromopyridine was removed by filtration. The solution was concentrated in vacuo and the resultant viscous liquid was dissolved in chloroform and extracted with saturated aqueous sodium carbonate and dried. The chloroform was removed in vacuo, leaving a yellow liquid which crystallized on standing. Impure 2-ethoxycarbonylamino-6-bromopyridine-1-oxide was recrystallized from cyclohexane, giving a 97.4% yield of off-white powder, m.p.=66.0°-67.5° C. A second recrystallization from cyclohexane raised the melting point to 66.5°-67.5° C.

| Elemental Analysis: | C | H | N |
|---|---|---|---|
| Calculated: | 36.80 | 3.47 | 10.73 |
| Found: | 37.12 | 3.53 | 10.78 |
| I.R.: N—H; 3.02, 3.21 | | | |
| C=O; 5.79 | | | |
| N—O; 7.92 or 8.25 | | | |

Step 3: A suspension of 1.3 g (0.0050 mole) of 2-ethoxycarbonylamino-6-bromopyridine-1-oxide in 17 ml (0.017 mole) of 1 M aqueous sodium hydrosulfide and 10 ml of ethanol was stirred at 65° C. for 2 hours. The reaction mixture was cooled and filtered, giving a 78% yield of the sodium salt of 2-ethoxycarbonylamino-6-mercaptopyridine-1-oxide, a white product which was recrystallized from aqueous ethanol.

| Elemental Analysis: | C | H | N | S |
|---|---|---|---|---|
| Calculated: | 40.68 | 3.84 | 11.86 | 13.57 |
| Found: | 40.93 | 3.75 | 11.88 | 14.29 |
| IR: N—H; 3.10, 3.23 | | | | |
| C=O; 5.89 | | | | |
| N—O; 7.79 | | | | |

EXAMPLE 4

Preparation of the sodium salt of 2-ethoxycarbonylamino-6-mercaptopyridine-1-oxide:

The procedure of Example 3 was repeated except that Step 2 relating to the oxidation to the pyridine-oxide was changed, whereby a chloroform solution of 2-ethoxycarbonylamino-6-bromopyridine was treated with m-chloroperbenzoic acid as the oxidizing agent for 9 days at room temperature, giving a 62% yield of 2-ethoxycarbonylamino-6-bromopyridine-1-oxide.

EXAMPLE 5

Preparation of the zinc salt of 2-ethoxycarbonylamino-6-mercaptopyridine-1-oxide:

0.236 g (0.00100 mole) of the sodium salt of 2-ethoxycarbonylamino-6-mercaptopyridine-1-oxide as prepared in Example 3 or Example 4 was dissolved in 15 ml water and 2.6 ml (0.00052 mole) of 0.20 M aqueous zinc nitrate was added dropwise while stirring the solution. A white solid precipitated immediately and was isolated by filtration giving a 68% yield of the zinc salt of 2-ethoxycarbonylamino-6-mercaptopyridine-1-oxide.

| Elemental Analysis: | C | H | N | S |
|---|---|---|---|---|
| Calculated: | 39.07 | 3.69 | 11.39 | 13.04 |
| Found: | 39.91 | 3.95 | 11.80 | 12.72 |
| IR: N—H; 3.01, 3.08, 3.25 | | | | |
| C=O; 5.75 | | | | |
| N—O; 8.06 | | | | |

EXAMPLE 6

Preparation of Bis[2-(6-ethoxycarbonylamino-1-oxopyridyl)] disulfide:

0.20 g (0.0084 mole) of the sodium salt of 2-ethoxycarbonylamino-6-mercaptopyridine-1-oxide prepared in accordance with either Example 3 or Example 4, was suspended in 8 ml water and stirred while adding 0.1 M aqueous potassium triiodide until the yellow color of excess triiodide persisted. An 89% yield of impure bis[2-(6-ethoxycarbonylamino-1-oxopyridyl)] disulfide precipitated and was recrystallized from acetonitrile to give a white solid, mp=186.0°–186.5° C.

| Elemental Analysis: | C | H | N | S |
|---|---|---|---|---|
| Calculated: | 45.06 | 4.25 | 13.14 | 15.04 |
| Found: | 45.03 | 3.98 | 13.00 | 14.89 |
| IR: N—H; 3.04, 3.11, 3.23 | | | | |
| C=O; 5.79 | | | | |
| N—O; 8.02 | | | | |

EXAMPLE 7

Preparation of Bis[2-(6-acetamido-1-oxopyridyl)disulfide]:

A suspension of 0.40 g (0.00217 mole) of 2-acetamido-6-mercaptopyridine-1-oxide, prepared as in Example 1, in 5 ml of water acidified to a pH of 2 with 2 M aqueous hydrochloric acid, was stirred while adding 0.1 M aqueous potassium triiodide until a permanent yellow color of triiodide was evident. The reaction product was filtered, giving a 70% yield of a tan product which was purified by recrystallization from glacial acetic acid, m.p.=249.0°–250.0° C.

| Elemental Analysis: | C | H | N | S |
|---|---|---|---|---|
| Calculated: | 45.89 | 3.85 | 15.29 | 17.50 |
| Found: | 45.52 | 3.72 | 15.35 | 18.43 |
| IR: N—H; 3.20 | | | | |
| C=O; 5.87 | | | | |
| N—O; 8.00 | | | | |

EXAMPLE 8

Preparation of 2-thoxycarbonylamino-6-benzylthiopyridine-1-oxide:

A suspension of 1.0 g (0.0038 mole) of 2-ethoxycarbonylamino-6-bromopyridine-1-oxide, as prepared in Step 2 of Example 3, in 25 ml of methanol containing equivalent amounts of benzyl mercaptan and sodium methoxide, is heated under reflux for 2 hours. The reaction mixture is diluted with 150 ml water and the impure product is collected by filtration. Recrystallization from ethyl acetate-cyclohexane gave white needles having a m.p. of 139.8°–140.2° C.

| Elemental Analysis: | C | H | N | S |
|---|---|---|---|---|
| Calculated: | 59.19 | 5.30 | 9.20 | 10.53 |
| Found: | 59.45 | 5.32 | 9.26 | 9.97 |
| IR: N—H; 3.04 | | | | |
| C=O; 5.76 | | | | |
| N—O; 7.95 | | | | |

From the elemental analysis and infrared spectral examination of the substituted amino-mercaptopyridine-oxide compounds and the intermediates thereof, the structure of each compound with above examples has been ascertained.

EXAMPLE 9

| Shampoo: | % |
|---|---|
| Sodium salt of 2-ethoxycarbonylamino-6-mercapto-pyridine-1-oxide | 1.0 |
| Potassium hexadecyl sulfate | 15.0 |
| Sodium coco-fatty acid monoglyceride sulfate | 15.0 |
| Coconut oil fatty acid diethanolamine | 5.0 |
| Lauric myristic monoethanolamide | 3.0 |
| Perfume | 1.0 |
| Lanoline esters | 1.0 |
| Sodium carboxymethyl cellulose | 0.2 |
| Glycerine | 2.0 |
| Water | Balance |

In lieu of the sodium salt of 2-ethoxycarbonylamino-6-mercaptopyridine-1-oxide, other salts wuch as the zinc salt, or the acylamino mercapto compound per se may be utilized. Similarly beneficial results are also obtainable by utilizing other shampoo formulations, based on nonionic or cationic detergents or other of the previously mentioned synthetic detergents instead of the mentioned combination of anionic detergents. A similar result is noted when the shampoo is based on soluble higher fatty acid soap. Usually, for shampoo applications, the milder of the mentioned detergents will be selected, so as to avoid unduly drying or embrittling the hair.

EXAMPLE 10

| Hairdressings: | % |
|---|---|
| (A) | |
| Light mineral oil | 72.0 |
| Isopropyl myristate | 22.0 |
| Lanoline | 2.0 |
| Lanolin esters | 1.5 |
| Perfume | 1.2 |
| Sodium salt of 2-acetamido-6-mercaptopyridine-1-oxide | 1.3 |
| (B) | |
| Light mineral oil, white deodorized | 45.0 |
| Stearic acid | 5.0 |
| Cetyl alcohol | 2.0 |
| Triethanolamine | 2.5 |
| Perfume | 0.7 |
| Zinc salt of 2-acetamido-6-mercaptopyridine-1-oxide | 2.0 |
| Water | 42.8 |

Approximately three cubic centimeters per application is used in treating human hair and scalp. This treatment may be repeated daily over a period of weeks. The compositions are especially useful with respect to diminishing fungal and bacterial counts and are particularly effective against *Pityrosporum ovale*, the yeast most frequently associated with dandruff, even in the presence of the sebum normally found on the hair and scalp.

In phase of the particular salts of 2-acetamido-6-mercaptopyridine-1-oxide of the above formulas, similar proportions, or variations in proportions within the ranges described in the specification, of other salts, e.g., the copper, nickel, chromium, trimethylcetyl ammonium, ammonium, alkanolamine and other such salts, may be employed to obtain substantially similar antimicrobial activities. It is noted that the bactericides are especially useful even in the normally oily environment of the scalp and hair and in the lipophilic phases of hairdressings.

Similar results are obtained when the mentioned bactericides are used in similar proportions in other cosmetics, e.g., hair setting compositions, "aerosol" hair sprays, hair dyes, skin creams, talcum powders and foot powders.

The invention has been described with respect to various illustrations and embodiments thereof. However, the invention is broader than the illustrations given and it will be evident to one of ordinary skill in the art that substitutes and equivalents may be employed within the invention concept.

What is claimed:

1. A mercaptopyridine-1-oxide compound having the following structural formula:

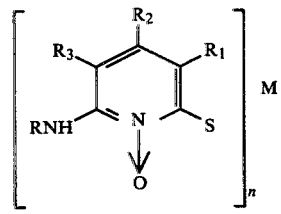

wherein R is selected from the group consisting of the acyl radical $R_oC=O$ and the alkoxycarbonyl radical $R_oOC=O$, where $R_O$ is a $C_1$-$C_6$ alkyl, aryl selected from the class consisting of phenyl, naphthyl, aralkyl where said alkyl portion has 1-6 carbons and halobenzyl; $R_1$, $R_2$ and $R_3$ are each independently selected from the group consisting of hydrogen, methyl, two of said terms may represent methoxy and the other hydrogen, one of said terms may represent ethyl, n-butyl, methoxy, ethoxy, phenyl, bromophenyl, chlorophenyl, trichlorophenyl, naphthyl, chlorobenzyl, dichlorobenzyl or furyl and the other two terms represent hydrogen; M is a mono-, di-, or trivalent metal selected from the group consisting of zinc, manganese, chromium, iron, copper, tungsten and nickel, and n is a whole number from 1 to 3.

2. A compound according to claim 1 wherein R is a $C_1$-$C_6$ acyl radical.

3. A compound according to claim 1 wherein $R_1$, $R_2$ and $R_3$ are all hydrogen.

4. A compound according to claim 1 wherein R is $C_1$-$C_6$ alkoxycarbonyl.

5. A compound according to claim 3 wherein R is $CH_3C=O$, M is zinc and n is 2.

6. A compound according to claim 3 wherein R is $C_2H_5OC=O$, M is zinc and n is 2.

* * * * *